(12) United States Patent
Santillan et al.

(10) Patent No.: US 8,764,625 B2
(45) Date of Patent: Jul. 1, 2014

(54) CONTOURED ELASTOMERIC BARRIER FOR BOWEL RETENTION AND METHOD OF USE

(75) Inventors: Antonio Santillan, El Paso, TX (US); Robert E. Bristow, Baltimore, MD (US); Joshua Liu, Naperville, IL (US); Gayathree Murugappan, Troy, MI (US); Anshuman Gupta, San Jose, CA (US); Brian G. Liu, College Station, TX (US); Sameer S. Manek, Naperville, IL (US); Michael R. Bisogno, Smithtown, NY (US); Kevin Yeh, Corvallis, OR (US); Vicki Zhou, Las Vegas, NV (US)

(73) Assignee: The Johns Hopkins University, Baltimore, MD (US)

( * ) Notice: Subject to any disclaimer, the term of this patent is extended or adjusted under 35 U.S.C. 154(b) by 718 days.

(21) Appl. No.: 12/989,253

(22) PCT Filed: Apr. 22, 2009

(86) PCT No.: PCT/US2009/002495
§ 371 (c)(1),
(2), (4) Date: Aug. 10, 2011

(87) PCT Pub. No.: WO2009/131676
PCT Pub. Date: Oct. 29, 2009

(65) Prior Publication Data
US 2012/0035414 A1 Feb. 9, 2012

Related U.S. Application Data

(60) Provisional application No. 61/125,219, filed on Apr. 23, 2008.

(51) Int. Cl.
*A61B 17/02* (2006.01)
(52) U.S. Cl.
USPC .......................................... 600/37; 600/208
(58) Field of Classification Search
USPC .................. 600/37, 201–246; 606/1, 191
See application file for complete search history.

(56) References Cited

U.S. PATENT DOCUMENTS

| 4,019,499 | A | * | 4/1977 | Fitzgerald ........................ 600/30 |
| 6,063,025 | A | * | 5/2000 | Bridges et al. ................ 600/208 |
| 2003/0139644 | A1 | | 7/2003 | Parsons et al. |
| 2005/0261545 | A1 | * | 11/2005 | Gellman et al. ................ 600/29 |
| 2007/0038032 | A1 | | 2/2007 | De Canniere et al. |

* cited by examiner

*Primary Examiner* — Charles A Marmor, II
*Assistant Examiner* — Catherine B Kuhlman
(74) *Attorney, Agent, or Firm* — Edwards Wildman Palmer LLP; Peter F. Corless; Richard B. Emmons (57) ABSTRACT

The invention provides a device for bowel packing having an essentially elliptical shape that is essentially symmetrical along a minor axis of the ellipse, and the device includes a notch located on the minor axis below the major axis. The device is composed of material comprising an elastomeric polymer and the device is appropriately sized for retaining the intestines of a mammal. The invention further provides methods of use of the devices of the invention for bowel packing. The invention further provides methods for increasing bowel packing speed, increasing effectiveness of bowel retention, decreasing the formation of post-operative intraperitoneal adhesions, and increasing temperature of the abdominal cavity during surgery by use of the device.

26 Claims, 7 Drawing Sheets

CONTOURED ELASTOMERIC BARRIER FOR BOWEL RETENTION AND METHOD OF USE

RELATED APPLICATIONS

This instant application is a 35 U.S.C. §371 U.S. national entry of International Application PCT/US2009/002495 (WO 2009/131676) having an International filing date of Apr. 22, 2009 which claims priority to U.S. Provisional Patent Application 61/125,219 filed Apr. 23, 2008, which is incorporated herein by reference in its entirety.

BACKGROUND

Abdominal and pelvic laparotomies require displacement and retention of bowels to create adequate exposure to the surgical site. When a section of bowel protrudes from the dressings into the surgical site, the entire bowel packing procedure must be completely redone. Continuous slipping of the bowels into the surgical field results in a waste of time and resources for the surgeon and extended anesthesia time for the patient.

The current packing procedure used in the operating room today is time-consuming relative to the overall priorities of events in a surgery. The surgeon first uses his hands to displace the bowels away from the surgical site. Intra-abdominal sponges and towels are then used to pack the bowels out of the way. Surgical cotton sponges are produced in a multitude of forms such as those described by U.S. Pat. Nos. 3,971,381; 4,490,146; 4,626,251; 4,205,680; 4,515,594; and 4,704,109. These cotton sponges are highly absorbent and ubiquitous in modern operating rooms. Finally, abdominal retractors are fitted over the dressings with gentle traction to hold them in place.

Bowel packing takes up to thirty minutes, and it must be repeated frequently during extended surgical procedures. Also, the surgical packs can be forgotten in the abdominal cavity. Furthermore, the cotton sponges used to pack the bowels are made of loose cotton fibers that remain in the abdominal cavity even after removal of the sponges. These fibers can promote peritoneal inflammation, a major cause of post-operative adhesion formation. Furthermore, the sponges tend to dry out over the course of the surgical procedure, becoming abrasive and adhesive to the bowels themselves, further contributing to the formation of adhesions, a leading cause of post-operative morbidity.

SUMMARY OF THE INVENTION

The invention provides devices for bowel packing having an essentially elliptically-shape, essentially symmetrical along a minor axis of the ellipse, wherein the ellipse has a minor axis having a length, a major axis having a length and a perimeter, wherein the device has a notch located on the minor axis below the major axis; and the device is composed of material comprising an elastomeric compound and the device is appropriately sized for retaining the intestines of a mammal.

In various embodiments of the device provided by the invention, the essentially elliptically-shaped devices include at least four radial notches in the perimeter, wherein
  (a) one or more radial notches arranged above the major axis, wherein each notch has a length from the center of the notch at the perimeter to a base of the notch, wherein the notch length is about 30% to about 40% of the length of the minor axis and each notch has a width at the perimeter of the ellipse that is about 10% to about 15% of a length of a major axis of the ellipse;
  (b) a second radial notch located on the minor axis below the major axis wherein the second notch has a length from the perimeter to a top of the notch that is about 30% to about 40% of the length of the minor axis and a width at the perimeter that is about 32% to about 42% of the length of the major axis;
  (c) two or more radial notches arranged left and right of the minor axis wherein each notch has a length from the center of the notch at the perimeter to a base of the notch is at least about 5-15% of the length of the major axis;
  wherein the device is composed of one or more elastomeric polymers having an elastic modulus of about 0.1 MPa to about 10 MPa and the device is appropriately sized for retaining the intestines of a mammal.

In various embodiments of the device provided by the invention, the ratio of the length of the minor axis of the ellipse to the length of the major axis of the ellipse is about 0.55 to about 0.65.

In certain embodiments of the invention, the devices can include one, two, three, four, five or more radial notches per (a) of arranged above the major axis, and two, four, six, eight, or more radial notches to the left of the minor axis and one radial notch to the right of the minor axis per (c), wherein the radial notches of (c) are located at or above the major axis and the device includes a bend near the line between two essentially symmetrically positioned radial notches of (c) near the line parallel with the major axis along a line near the top of the bottom radial notch. This bend in the device, as well as the curvature and flexibility of the flaps created by the notches make the devices of the invention essentially concave.

The devices provided by the invention include radial notches of essentially any shape that are independently selected. Notch shapes include, but are not limited to V-shaped, U-shaped, and bell-shaped.

The invention provides devices having varying thicknesses. In an embodiment, the portion of the device at an intersection of the major axis and the minor axis is greater than the thickness of the device at the perimeter. The greater thickness of the device in the central portion for contacting the bowel provides greater rigidity, whereas the thinner, more flexible flaps allow for proper positioning of the device within the gut.

In various embodiments, the invention provides a device includes a coating. The coating can be useful to prevent sticking of the device to the bowel or to provide any other desirable surface property to the device. Many appropriate coatings can be selected by one of skill in the art.

The invention provides devices including an essentially rectangular body including a first long edge opposite a second long edge and a first short edge and a second short edge wherein the first and second short edge separate the long edges; wherein
  a) the first long edge is contiguously joined along the length of the first long edge to a top flap having a height and a width, wherein the top flap includes a cutout from an edge of the flap opposite the long edge of the body to which the flap is attached, wherein the depth of the cutout is at least 80% of the height of the top flap;
  b) the second long edge is contiguously joined along the length of the second edge to a bifurcated bottom flap wherein each half of the bifurcated bottom flap has a height and a width wherein the height and the width of each half flap is essentially the same as the height and width of the other half flap, and the width of the flap extends about 10 to 20% beyond the length of the long edge of body of the device on each side of the long edge, wherein the bottom flap is bifurcated by a cutout on an edge of the flap opposite the long edge of the body to which the flap is attached wherein the width of the cutout is about 30% to about 55% of the length of the long edge of the device and the cutout is centered along the long edge of the body of the device, and the height of the cutout is about 25% to about 40% of a height of the device at the tallest point perpendicular to the first long edge of the body; and c) a first short edge contiguously joined along the length of the first edge to a first side flap and a second short edge contiguously joined along the length of the second short edge to a second flap wherein the first side flap and the second side flap have a height and a width, and each the height and the width of the first side flap are about the same as the height and the width of the second side flap; wherein the width of each side flap is about 10-20% of an overall width of the device, wherein the lower edge of each side flap forms a smooth edge with a bottom half flap; the device is appropriately sized for bowel packing in a mammal; and the device is composed of one or more elastomeric polymers having an elastic modulus of about 0.1 MPa to about 10 MPa.

In an embodiment, the ratio of the short edge of the rectangular body to the long edge of the rectangular body of the devices provided by the invention is about 0.2 to about 0.3.

In an embodiment, the devices provided by the invention are essentially concave. The concave shape of the device can be provided in part by a bend near the line that forms the top of the rectangular body, for example along a line near the top of the notch of (b).

The devices provided by the invention include radial notches of essentially any shape that are independently selected. Notch shapes include, but are not limited to V-shaped, U-shaped, and bell-shaped.

The invention provides devices having varying thicknesses. In an embodiment, the portion of the device at an intersection of the major axis and the minor axis is greater than the thickness of the device at the perimeter. In certain embodiments, the thickness of the bifurcated bottom flap is greater than the thickness of the top flaps. The greater thickness of the device in the central portion for contacting the bowel provides greater rigidity, whereas the thinner, more flexible flaps allow for proper positioning of the device within the gut.

In an embodiment, the invention provides a device includes a coating. The coating can be useful to prevent sticking of the device to the bowel or to provide any other desirable surface property to the device. Many appropriate coatings can be selected by one of skill in the art.

The invention provides devices composed of any material having appropriate physical properties as provided herein. Exemplary materials for use for manufacture of the device include, but are not limited to elastomeric compounds including various forms of silicone, liquid silicone rubber (LSR), polydimethylsiloxane (PDMS), styrene butadiene rubber, styrene butadiene styrere (SBS) rubber, nitrile rubber, and polychloroprene. Devices of the invention can also include other materials such as fibers encased within the elastomeric compound or radio-opaque substances. Devices of the invention can be manufactured from composites of elastomeric materials.

The invention provides methods of use for the devices of the invention for retaining the bowel outside of the surgical field during abdominal surgery. Methods include contacting a bowel of the subject with the device to retain the bowel away from a surgical site in a subject, and maintaining the device against the bowel during the abdominal surgery. In embodiments of the device including a concave face, the bowel is contacted with the concave face of the device.

The methods of use of the devices of the invention provide advantages over the use of sponges and laparotomy packs, for example by increasing intra-abdominal temperature during the abdominal surgery and reducing the time required for bowel packing relative to the time required with the use of laparotomy pads.

DEFINITIONS

As used herein, "appropriately sized for bowel packing in a mammal" is understood as being dimensioned to allow for insertion into the abdominal cavity of a mammal including having an face compatible for contact with the bowel for packing and retention, and flaps of a length and width to allow for the device to be retained in the abdominal cavity and prevent protrusion of the bowel into the surgical area. For example, in adult humans, the size of the abdominal cavity is about 3.9 to 5.8 inches in the transverse plane at the height of the base of the ribs and about 7.6 to 11.3 inches in the coronal plane at the height of the base of the ribs. An appropriately sized device for bowel packing in a mammal having such dimensions is about 5.2 to about 7.5 inches overall height (from ventral to dorsal sides of the abdominal cavity upon placement) and about 8.7 to about 12.5 inches in overall width (from lateral side to lateral side of the abdominal cavity upon placement). The face for contacting the bowel is rectangular with curved corners about 6.26 to about 8.99 inches wide and about 2.60 to about 3.74 inches high with a semi-circular cut-out centered on a long side of the rectangle having a diameter of about 2.80 to about 4.02 inches to accommodate the spine. Therefore, an appropriately sized device is overall somewhat larger than the dimensions of the abdominal cavity of the mammal in the transverse plane in which the device is to be used, having a face that is somewhat smaller than the dimensions of the abdominal cavity in the transverse plane. Further, the device is sufficiently small to allow for compacting of the device for insertion into an incision, and manipulation of the flaps to position the device in the mammal snugly securely against the bowel.

As used herein, "bowels" is used generically to include bowel, intestine, and other abdominal organs that would need to be displaced in the abdominal cavity to allow for abdominal surgery. It is understood that the specific organs to be displaced will depend on the specific surgery to be performed.

As used herein, "cephally" is understood as towards the head of the subject.

"Compression" as used herein is understood as the manual folding or rolling of the device in a manner reasonable for insertion into the abdomen during surgery. This involves folding no more than a single layer, or rolling no more than 360 degrees, or twisting typically no more than 180 degrees.

As used herein, "contiguously joined" is understood to mean that the two portions of the device are attached along the length of the edge as described. A contiguously joined flap can extend beyond the length or width of the body of the device.

"Distal" as used herein is understood as the surface of the device away from the bowel. When inserted in a human subject, the distal face of the device will point towards the feet and away from the head of the subject.

"Dorsal" as used herein is understood as being towards the back of the body of the subject.

As used herein, "elastomeric compound" is understood as an elastic compound having an appropriate flexibility/rigidity, tear resistance, and sterilization resistance for use in the devices of the invention. Elastomeric compounds for use for manufacture of the device of the invention are sufficiently flexible to prevent damage from occurring to tissues or organs by contact with the device when in a non-compressed state. Elastomeric compound as used herein typically refers to an elastomeric polymer. The monomers that link to form the polymer are typically made from of carbon, hydrogen, oxygen and/or silicon. Examples of elastomeric polymers include Liquid Silicone Rubbers (LSR) and Silicone Encapsulants. In a preferred embodiment of the invention, the elastomeric polymer is a "silicon polymer". A "silicon polymer" is understood as any silicon-based polymeric material that has the appropriate flexibility/rigidity, tear resistance, and sterilization resistance for use in the devices of the invention. In a preferred embodiment, the silicon polymer is optically clear. Elastomeric compounds for use in the device of the invention include, but are not limited to silicone, liquid silicone rubber (LSR), polydimethylsiloxane (PDMS), styrene butadiene rubber, styrene butadiene styrere (SBS) rubber, nitrile rubber, and polychloroprene (Neoprene). In a preferred embodiment, silicon polymer is polydimethylsiloxane (PDMS) a silicon-based organic polymer. PDMS is optically clear, and is generally considered to be inert, non-toxic and non-flammable. It is occasionally called dimethicone and is one of several types of silicone oil (polymerized siloxane).

Figure 1A:
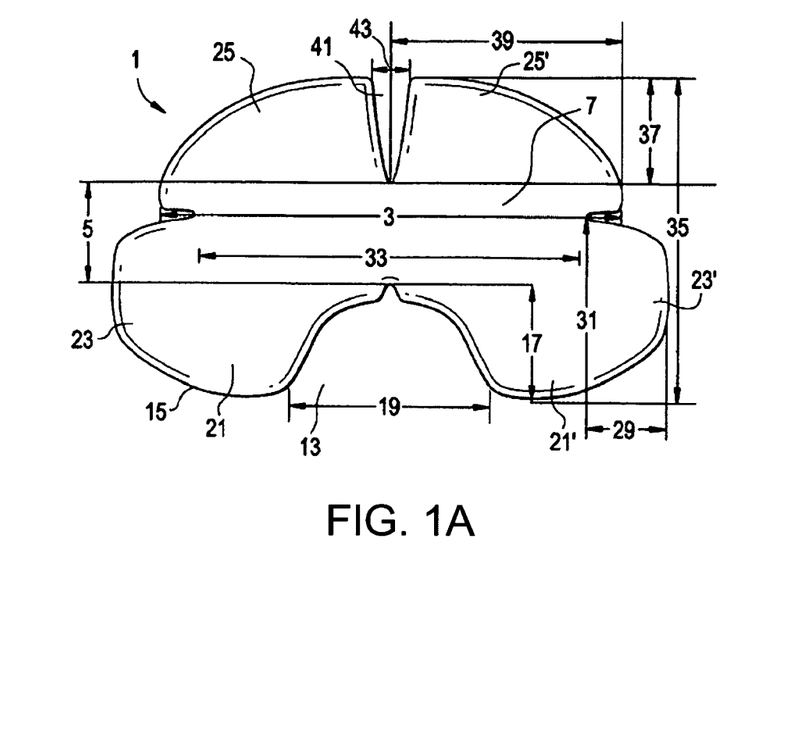
FIGS. 1A to E show A) a front view of an embodiment of the device of the invention, B) a side view of an embodiment of the device of the invention, C) top view of an embodiment of the device of the invention, D) alternative side view of an embodiment of the device of the invention, and E) a front view of the device overlaid with an ellipse and a rectangle.

As used herein, "essentially" typically as in "essentially elliptical" or "essentially rectangular" is understood as approximating the stated shape to facilitate description of the device. For example, the device as shown in the front view in FIG. 1A is essentially elliptical meaning that the shape of the device is obviously longer in one direction than the other, and that all of the corners are rounded. When the central portion of the device is stated to be "essentially rectangular" it is understood that removal of the flaps wherein the flaps are defined by the point of the notch closest to the center of the device, would result in a rectangle. "Essentially symmetrical" is understood that as the device is for insertion into an essentially symmetrical cavity, i.e., the abdominal cavity (left-right symmetry), the device a flap or notch on the right side would have a corresponding flap or notch on the left side. A notch that falls on the medial sagittal plane of the device has a symmetrical shape about the plane. "Essentially concave" is understood as a central portion surrounded by flaps wherein all of the flaps point in the same general direction defining a central space, and does not require a continuous curvature.

"Lateral" as used herein is understood as being towards the sides of the body of the subject.

"Medial" as used herein is understood as the midline of the body in the sagittal plane of the body (i.e., along the spine).

"Proximal" as used herein is understood as the face of the device closer to the bowel to be enclosed, specifically the face of the device closer to the bowel. When inserted in a subject, the proximal face of the device points cephally.

As used herein, "rigidity" is understood as the inflexibility of the main body of the device, excluding the flaps, that allows the body to support the bowels without collapsing. Materials with a Young's modulus of about 300 KPa to about 900 KPa and a yield point over 500 KPa are appropriate.

"Smooth edge" as used herein is understood as an edge having a continuous, even surface that does not cause resistance to sliding. Typically a smooth edge is understood as a continuous straight or rounded edge.

In the "Trendelenburg position" the body is laid flat on the back (supine position) with the feet higher than the head. The specific angle to be used is a matter of choice of the surgeon.

"Ventral" as used herein is understood to mean towards the front of the body.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. Further, ranges provided herein of fractional numbers, includes all of the values with the same number of significant figures therebetween. For example, if the value is provided in hundredths, the range includes all values at $1/100^{th}$ intervals such that the range 8.15 to 8.25 is understood to include 8.15, 8.16, 8.17, 8.18, 8.19, 8.20, 8.21, 8.22, 8.23, 8.24, and 8.25.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

Any features, devices, or methods provided herein can be combined with one or more of any of the other features, devices, and methods provided herein.

DETAILED DESCRIPTION AND PREFERRED EMBODIMENTS

The devices of the invention allow for a reduction in operating room time, decreasing cost; a reduction in anesthesia time, reducing surgical risk to the patient; and a reduction in post-operative morbidity associated with the use of surgical sponges used in current procedures. Specifically, the devices of the invention to encompass bowels without leaving behind particulate matter as occurs with sponges.

The invention provides a device that is preferably a continuous, one-piece device that permits retention of the internal organs away from the surgical site during open abdominal surgeries to prevent obstruction during open surgeries. The device is preferably essentially symmetrical relative to the sagittal plane, as the abdominal cavity is essentially symmetrical relative to the sagittal plane. The device is essentially elliptical shape as the device is designed to fit snugly in the interior of the abdominal cavity which has an essentially elliptical shape. The top portion of the ellipse for contacting the ventral side of the subject is typically more narrow than the bottom portion of the ellipse for contacting the ventral side of the subject. The ventral side includes a cut-out in the center of the bottom edge to accommodate the spine of the subject.

In an embodiment of the invention, the device is manufactured from a clear elastomeric compound, preferably a polymer such as a silicon polymer device having an overall essentially elliptical shape, with a cut-out to accommodate the spine. The device is preferably essentially concave. The device is made of one or more elastomeric compounds that have physical properties (e.g., elastic modulus, flexibility/rigidity, tear resistance, etc) to allow the device to be easily compressed for insertion into a subject through an incision, but rigid enough to expand once placed in the abdominal cavity and to retain the bowel in conjunction with one, preferably two, retractors. The measurement of the device is about the same as the size of the interior of the abdominal cavity or a bit larger, preferably about 2% larger, about 5% larger, about 7% larger, about 10% larger, about 12% larger, or about 15% larger. The relative size of the device in each dimension as compared to the abdominal cavity is determined independently. The device includes at least one cut-out, preferably a wide cut-out such a semi-circular, U-shaped, or bell-shaped cut out appropriately sized to accommodate the spine of the subject in which the device is to be used, about 30% to about 40% of the overall width of the device, and about 30-40% of the overall height of the device. When positioned in the abdominal cavity of a subject, the device is typically held in place by retractors. A sufficient portion of the edges of the device are in contact with the interior of the abdominal cavity to prevent protrusion or leakage of the bowel into the surgical site for at least one hour. Methods to test devices for to determine if they meet the criteria of the invention are routine and known in the art. Methods are provided in the examples below.

The device can include further radial notches along the edge of the device creating tabs between the notches to be tucked cephally to facilitate positioning of the device in the bowel. The notches can be essentially any shape, e.g., V-shaped, U-shaped, bell-shaped around the periphery of the device. The notches are of a sufficient depth such that when all of the flaps created by the notches are folded in, the body of the device is slightly smaller than the abdominal cavity in which the device is to be used. The length of the notches should be limited so as to retain a face on the device for contacting the bowel that is at least about 60% of the height of the abdominal cavity (ventral to dorsal) and at least about 75% of the width of the abdominal cavity (lateral side to lateral side). Typically, the shorter the notches, and therefore the shorter the flaps created by the notches, the more rigid the face of the device should be. The greater the number of notches, the more narrow the notches should be to prevent the formation of gaps that can allow the bowel to leak into the surgical field. Moreover, the number of notches is sufficient to allow the flaps to be positioned inside the subject, but few enough to maintain sufficient rigidity in the flaps to retain the device in position in the subject.

In a preferred embodiment, the device includes a wide notch in the bottom edge of the device, creating a bifurcated flap, to provide space for the spine, and one or more relatively deep notch(es) in the top edge of the device, typically arranged symmetrically relative to the medial sagittal plane. The deep notch in the top flap allows the top flaps to be tucked in over the bowel on the ventral side of the subject and to provide a point of compression or expansion at the top of the device. The bottom of the top flaps is further defined by relatively shallow and narrow notches in the sides of the device. The side notches facilitate bending of the device to allow the top flaps to be tucked in, and for the edges of the top flaps to be pulled in towards the center of the device towards the coronal plane. Also defined by the side notches, and continuous with the bottom flaps, are two side flaps. Additional notches can be present in the side flaps. The side flaps are tucked into the sides of the abdominal cavity towards the coronal plane, and the bottom portion of the flaps is tucked cephally to retain the bowel. Bending and positioning of the flaps is preferably facilitated by manufacturing the device such that the central body of the device for placement against the bowel is more rigid than the flaps. Increased rigidity is typically accomplished by making the central portion of the device thicker than the flaps. However, increased rigidity can also be accomplished by the use of a different elastomeric compound, including a composite compound or material, including incorporation of fibers or other materials into the device to increase rigidity. Rigidity can also be increased by the use of a frame partly or completely surrounding the central portion of the device. Also, the device preferably has an overall curved shape with the concave face of the device contacting the bowel and facing cephally surrounded by one or more flaps that can be tucked around the periphery of the abdominal cavity to point cephally.

The device includes a main body contoured to fit the interior of abdominal cavity, having an overall essentially elliptical shape with an approximately semi-circular or bell-shaped cut-out creating a bifurcated flap to accommodate the spinal and pelvic structures. The body of the device and the peripheral flaps are appropriately sized to allow for packing of the bowel in a range of abdominal cavity shapes and sizes as found in vivo. The overall size of the device is slightly larger than the cross-section of the interior of the abdominal cavity where it is to be applied, about 2%, about 5%, about 7%, about 10%, about 12%, or about 15%, such that the device will expand and exert slight pressure against the interior of the abdominal muscular wall. The device can be held in place by tension; however, use of at least one, preferably two or more retractors to retain the device in position is preferred.

The devices of the invention are preferably made in different sizes for use in patients of different sizes (e.g., children and adults). Further, it is understood that the device can be made for use in non-human animals, for example in pets and other domesticated and non-domesticated animals of value to humans, for example cats, dogs, non-human primates, animals used for medical research including surgical research such as pigs, zoo animals, etc. The disclosure provides information regarding the preferred sizes of the device for use in adult humans, and the size of the abdominal cavity of adult humans. Provided with this information, a device can be made that is appropriately sized for use in mammals other than human adults. Such modifications are well within the ability of those of skill in the art.

The peripheral flaps, continuous with the main body and projecting from the periphery of the device aid in the retention of the bowels by forming a pliable seal between the device and a range of differently sized and shaped abdominal walls and spinal columns, with larger flaps capable of being pulled across exposed tissue to increase the area covered by the device. The flaps may include slits where necessary, such that when the main body is folded, compressed, or rolled, the flaps may be folded, compressed, or rolled in an orthogonal direction. Slits in the flaps run radially from the main body, such that when the device is inserted into the abdominal cavity in the final position, the flaps overlap where necessary to prevent protrusion of bowels into the surgical field. The flexibility of the fit of the device in the abdominal cavity by an increased number of slits is balanced by the rigidity provided by having extended flaps. In an embodiment, only the flaps for positioning against the ventral and dorsal sides of the abdominal cavity include slits. In an embodiment, the flaps independently include 0, 1, 2, 3, or 4 slits. The rigidity of the body must be balanced with the length and number of the flaps.

The material for the body of the device is of sufficient flexibility to permit folding, compressing, or rolling of the device to allow for insertion through a retracted incision as small as 10 cm in diameter, while being of sufficient rigidity to expand after folding, compression, or rolling, and retain the bowels for the duration of a surgical procedure when used in conjunction with retractor blades. The device is manufactured from one or more elastomeric compounds, preferably an elastomeric polymer such as silicone or polydimethylsiloxane. The device can be composed of more than one compound, including composites of one or more elastomeric compounds or polymers, optionally further in conjunction with fiber reinforcement, wherein the fibers are completely contained within the elastomeric compound to modulate structural properties of the device, or to provide other properties to the device. In an embodiment, the device can further include radio-opaque fibers or other radio-opaque materials to make the device x-ray detectable.

A preferred material for the invention is silicone based organic polymer, Polydimethylsiloxane (PDMS), which is nonabrasive, inert, and nontoxic in nature. PDMS is optically clear, generally considered to be inert, non-toxic and non-flammable, and flexible enough to allow conformation of the device to varying abdominal cavity sizes, yet robust enough to allow interfacing of retractor blades to retain the device in the desired position. PDMS has been assigned CAS number 63148-62-9, and is occasionally called dimethicone. The chemical formula for PDMS is $(H_3C)_3SiO[Si(CH_3)_{20}]_nSi(CH_3)_3$, where n is the number of repeating monomer $[SiO(CH_3)_2]$ units.

In a preferred embodiment, the main body is composed of an inner core of Sylgard® 184 (Dow Corning) polydimethylsiloxane polymer between 8 and 14 mm in thickness, to provide rigidity to the main body, encased in a layer of Sylgard® 186 to confer improved tear-resistance and durability to the device. Flaps are made of a tear resistant silicon polymer, with sufficient flexibility to allow for adjustment of the flaps in the abdominal cavity, while providing sufficient rigidity to retain the device in place. Preferred peripheral flap materials include Sylgard® 186 between 2 and 8 mm in thickness, projecting from the main body at angles of between 20 and 60 degrees, and decreasing in thickness with distance from the main body.

When using more than one elastomeric compound for manufacture of the device, the compounds can be used together in any manner. For example, a polymer with the desired rigidity can be coated with a polymer having greater smoothness. The body of the device can be composed of one polymer, and the flaps can be composed of one or more other polymers to provide varying amounts of rigidity to the body of the device and the flaps.

The devices of the invention can also include other components such as coatings to reduce sticking of the device to the bowel by coating with polymers, particularly biocompatible polymers, of with commercially available coatings such as Seprafilm®. The coatings may be drug eluting. The coatings may be applied by bulk application, molecular conjugation with the body material, or through nanostructure formation. Examples of possible coatings include: SEPRAFILM®, INTERCEED®, SIROLIMUS®, PACLITAXEL®, EVEROLIMUS®, TRANILAST®, DACRON®, SPRAY-GEL®, ADHIBIT®, TEFLON®, PRECLUDE® Gore, SyntheMed REPEL-CV®, DuraGen, ADCON™ P (Gliatech), REPEL™ and RESOLVE™ (Life Medical Sciences), INTERGELT™ (formerly LUBRICOAT®), icodextrin, hyaluronic acid, heparin, dextran, tissue plasminogen activator, corticosteroids, non-steroid inflammatory drugs (NSAIDS) such as ibuprophen, chondroitin sulfate, carboxymethylcellulose, dexamethosane, tissue plasminogen including recombinant tissue plasminogen, oxyphenbutazone, collagen, collagen inhibitors, polylactic acid, polyglycolic acid, alginic acid, polycaprolactone, glycosaminoglycans, polyethylene oxide (PEO), polyethylene oxide-polypropylene oxide copolymer in any monomeric ratio (PEG-PPO-PEG), hydroxy ethyl methyl acrylate (HEMA), poly(N-isopropylacrylamide) (NIPAAm), polytetraflouroethylene (PTFE), polyesters, and silane, or modification by radio frequency gas discharge (RFGD), and radiation grafting. polytetrafluoroethylene (PTFE), polylactic acid, polyglycolic acid, alginic acid, polycaprolactone, glycosaminoglycans, HEMA, ePTFE, polyesters, carboxymethylcellulose, dexamethasone, tissue plasminogen including recombinant tissue plasminogen, oxyphenbutazone, corticosteriods, icodextrin, hyaluronic acid, hyaluronan, and collagen inhibitors. Additionally, the device surface can be modified by silanization, RFGD, or radiation grafting.

Alternatively, devices can be coated with agents, for example, anti-microbial agents such as anti-viral agents or anti-bacterial agents. The use of such agents may be useful for the protection of the subject as well as the surgical staff and to reduce the possibility of transmission of infection from subjects infected with HIV, hepatitis, especially drug-resistant forms of hepatitis, methicillin resistant staphylococcus aureus (MERSA), etc.

The flexibility of the materials used to make the device also allow for a single size device to be used in subjects through a range of sizes. However, in a preferred embodiment, the devices are made in different sizes for use in different subjects. The multiple flapped structure of the invention creates surfaces for retaining the organs within the preferred location of the abdominal cavity and away from the surgical site. Determination and selection of a device of an appropriate size for use with a particular subject is well within the ability of those of skill in the art.

The contour of the device conforms to the sides of the abdominal cavity, in an essentially concave shape proximal to the bowel when inserted, to prevent protrusion of the bowels into the surgical field and allows the bowels to be scooped cephally in a single, smooth motion. The top flap (for positioning adjacent to the ventral side of the subject) is preferably designed with a one or more vertical slits to fold over the top of the bowels in the abdominal cavity and prevent the bowels from leaking over the top of the device, obscuring the surgical field. Preferably the bottom flaps further include at least one slit or opening, both to provide space for the spine, and to allow for the device to conform to the abdominal cavity. The conforming of the device to the sides and top of the abdominal cavity by the side and top flaps allows for bowel retention for the duration of the surgical procedure and simplify the packing procedure.

Further, in a preferred embodiment, the devices of the invention are made of a clear material which allows the bowels to be monitored continuously throughout the procedure, an advantage not allowed by the laparotomy packs currently being used. Further, the use of an elastomeric material provides for retention of both moisture and warmth in the abdominal cavity as compared to packing methods using surgical sponges as demonstrated herein.

Insertion of the Invention into the Abdominal Cavity:

Insertion of the device into the patient is preferably done manually by the surgeon. The device is first compressed sufficiently to allow for insertion through the retracted incision in the patient. The device is preferably oriented prior to insertion so that the top flaps will be pointed towards the ventral side of the patient and the concave proximal face of the device will face cephally after decompression. Insertion can be facilitated by placing the patient in the Trendelenburg position, a vertical tilt, typically about 15°, with the feet higher than the head. Once the device is inserted, it expands against the abdominal side walls and can be used to scoop the bowels cephally by placing the center of the device against the bowel and adjusting the flaps cephally. Once this has been completed, the device is secured in place using retractor blades. The exact position of the device will depend on the location of the incision and the choice of the surgeon. The exact method of insertion of the device is not a limitation of the invention. It is understood that a device of the invention can be used for packing other organs clear a surgical field. The specific use of the device is not a limitation of the device of the invention.

Removal of the Device from the Abdominal Cavity:

When removing the device from the patient, the surgeon supports the device with one hand while the retractor blades are removed. The surgeon places the index finger of either hand into the notch between the bottom flaps, pulling the device upward while compressing it with the palms. The exact method of removal of the device is not a limitation of the invention.

FIGS. 1A to E show an embodiment of the device 1 of the invention. Measurements are provided in parenthesis to approximate the preferred medium size of the embodiment of the invention. The medium size device of the invention for use in a human adult can vary up to about 5% from the base measurement provided in the detailed description of FIG. 1 below, and the measurement provided should be understood to include this variation within the range of about 0 to about 5% (i.e., about 1%, about 2%, about 3%, about 4%, or about 5%). The device for use in a small adult human is within the range of about 75% to 85%, preferably about 80% of the base dimensions provided for the medium size device. The device for use in a large adult human is within the range of about 110% to 120%, preferably about 115%, of the base dimensions provided for the medium size device. One of skill in the art can readily perform the calculations required to determine the appropriate size of the device based on the disclosure provided herein.

The specific size of the device is not a limitation of the invention. The limitation of the size of the device is that it must be appropriately sized for insertion into the abdominal cavity of a subject, preferably a human subject, for bowel retention. The invention provides a device, more preferably a single piece device, including a body having a two long edges opposite each other on the body, and two short edges between the long edges on opposite sides of the body. The device further includes two top flaps on a long edge of the body, two side flaps on short edges of the body adjacent to one long edge, and a cut-out on the long edge opposite the long edge with the flaps. The device has a smooth proximal surface for placement against the bowel of the subject to displace the bowel cephally and expose abdominal organs for surgery.

As shown in the front view in FIG. 1A of an embodiment of the device 1, the essentially rectangular central portion 207 of the device has a width 3 (7.82 inches) and a height 5 (3.63 inches), and in the embodiment shown is the essentially rectangular portion of the device defined by a first long edge at the base of the notch separating the first and second top flap of the device, and a second long edge defined by the top of the bell-shaped cutout in the bifurcated bottom flap, and short edges perpendicular to the long edges, adjacent to the paired notches on opposing sides of the device that separate the top flap from the body of the device. The central rectangle 207 of the device is not a structural element of the device, but instead is used in the description of the device herein to allow for the description of the size and position of various components of the device. The body 7 of the device serves mainly to support the bulk of the bowel and intestines on the concave proximal face 9, and also interfaces with retractor blades currently used in laparotomies on the convex distal face 11. The standard retractor blade setup uses two blades that interface with the lateral sides of the body. There is a bell-shaped cut 13 with in the bottom edge 15 (for placement towards the ventral wall of the abdominal cavity), opposite the edge including the top flaps. The bell shaped cut has a height 17 (2.28 inches) and a base width 19 (4.00 inches). The cutout is provided to accommodate the ventral medial part of the body in the sagittal plane, and designed to conform to, and provide space for, the spinal cord. The cut also creates two flaps 21 and 21' on the bottom edge 15 of the device. Upon insertion, two side flaps 23 and 23' contact the lateral sides of the abdominal cavity and two top flaps 25 and 25' contact the ventral side of the abdominal cavity. These flaps and the body of the device are one contiguous structure, preferably made from a single piece of elastomeric material, preferably a silicon polymer. The side flaps curve upward from the proximal face of the body of the device (3.71 inches) in the embodiment shown for a desired length 27 and each have a width 29 (1.55 inches) and a height 31 (3.63 inches). In an alternative embodiment, the upward curve of the flaps is shorter, but the material from which the flaps is somewhat more rigid to retain the device in the abdominal cavity. The dimensions of the device, including the body and the side flaps are width 33 (10.92 inches), height 35 (6.53) and depth 27 (3.71 inches). The side flaps serve to aid the body of the device in containing bowels that may protrude around the sides of the device in the abdominal cavity otherwise. The top flaps have a height 37 (2.90 inches) and a width 39 (4.75 inches) There is also a U-shaped cut 41 to separate the two flaps 25 and 25' having a base width 43 (0.86 inches). The top flaps lean towards the proximal face of the body of the device at an angle 45 preferably at an angle in a range of about 145° to 155° relative to the body 7 of the device. The angle of the flaps to the proximal face becomes more oblique as the length of the flaps becomes shorter to maintain the overall height of the device. The purpose of the top flaps 23 and 23' is to help secure the bowels on the ventral side of the subject. The device preferably has varying thicknesses throughout the body and flaps. The thickness of the body and flaps is consistent between the varying sizes of the device, however, the specific thicknesses of various portions of the device depends on the specific material used for the device. When the device is made from PDMS and the flaps are sized as provided in the detailed embodiment, the top flaps 25 and 25' are the thinnest, within the range of about 0.14-0.16 inches; the body 7 is the thickest portion, within the range of about 0.60 to about 0.68 inches; and the side flaps 23 and 23' have an intermediate thickness, within the range of about 0.30 to 0.34 inches. Modifications of thickness of various portions of the device is within the ability of those of skill in the art, and depend on a number of factors discussed herein, including, but not limited to the specific material or materials from which the device is made.

Figure 1B:
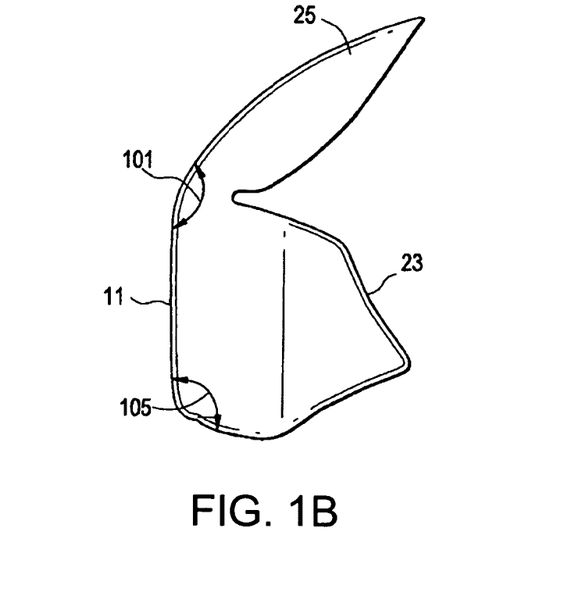

FIG. 1B shows an embodiment of the device as the various portions would be positioned when placed in a supine subject and the subject was viewed from the lateral side. The convex face of the device 11 is shown and the concave face of the device is hidden by the top 25, side 23, and bottom flaps. The top flap 25 bends cephally at an angle 101 of about 140° to about 160° to the concave face of the device. In the embodiment shown, the bottom edge of the bottom flap having a width approximating the height of the bell-shaped cut in the bottom flap folds towards the concave face of the device at an angle 105 of about 95° to 115° with the concave face of the device with the flap lengths shown. With shorter top and bottom flaps, the angle of the flaps to the proximal face of the device becomes more oblique. The side flaps are also positioned cephally towards the concave face of the device.

Figure 1C:
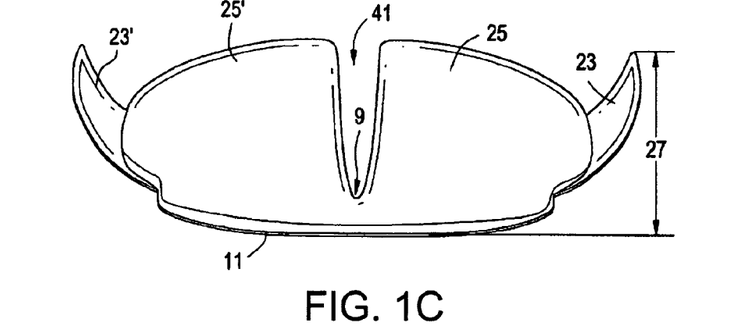

FIG. 1C shows an alternate view of an embodiment the device as it would be positioned when placed in a supine subject and the subject was viewed looking down at the subject from above through the ventral side. The top 25, 25' and side 23, 23' flaps are angled towards the proximal face 9 of the device.

Figure 1D:
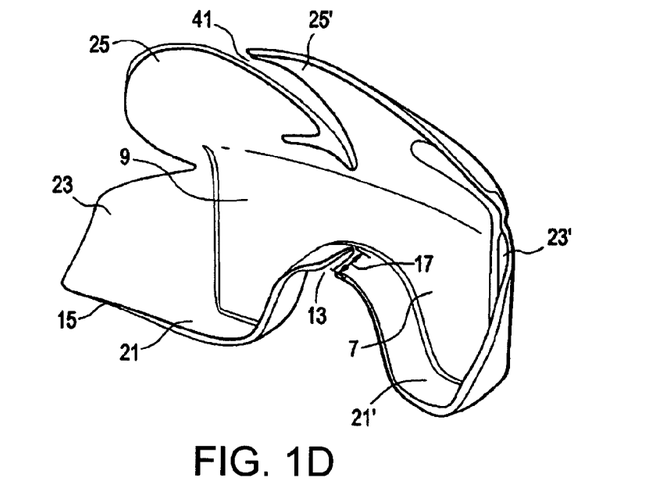

FIG. 1D shows an alternate view of an embodiment of the device as it would be positioned when placed in a subject and viewed at a oblique angle looking from the shoulder towards the feet of the subject. The top 25, 25', side 23, 23', and bottom 21, 21' are pointing cephally to define the concave proximal face 9 for contact with the bowel. In the embodiment shown, the relative thicknesses of the various portions of the device are shown. The varying thicknesses of the portions of the device allow for varying amounts of rigidity or flexibility. The body 7 of the device is the thickest portion of the device, providing substantial rigidity in the portion of the device for contact the bowel. The rigidity of the body may be modified by the inclusion fibers completely enclosed within the elastomeric material of the body, or may be surrounded partially or completely by a frame to modify the rigidity. The decrease in thickness of the device in the flaps facilitates manipulation of the flaps. The bottom and side flaps of the device are somewhat thicker than the top flaps in the embodiment shown as the patient will likely be in a supine position and the bottom flaps will need to be sufficiently rigid to be retained in position to reduce or eliminate inadvertent contact with the spine. In a preferred embodiment, after proper insertion, the device does not contact the spine. The top flaps of the device are thinnest an most flexible providing the user with options regarding exact placement of the device and providing allowance for variations in size between subjects.

Figure 1E:
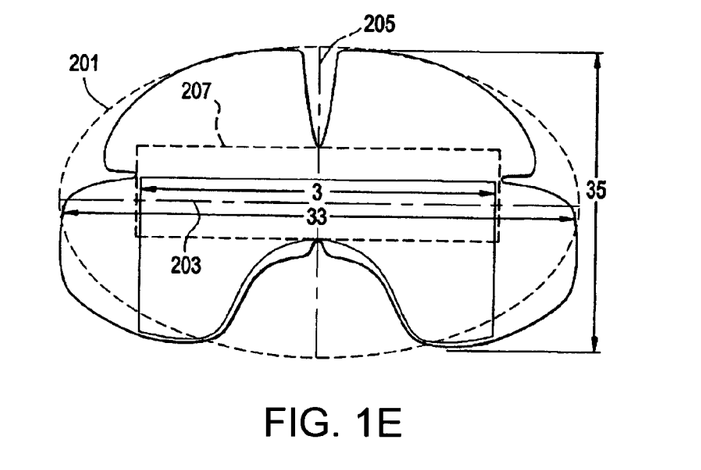

FIG. 1E shows an overlay of an embodiment of the device with an ellipse 201, with the major axis 203 and minor axis 205 shown for determining relative sizes of various portions of the device. The Figure also shows an overlay of an embodiment of the device with a rectangle 207 defining the body of the device for determining the relative sizes of various portions of the device. The length of the flaps will determine the angle at which the flaps are positioned relative to the proximal face of the device.

Figure 2A:
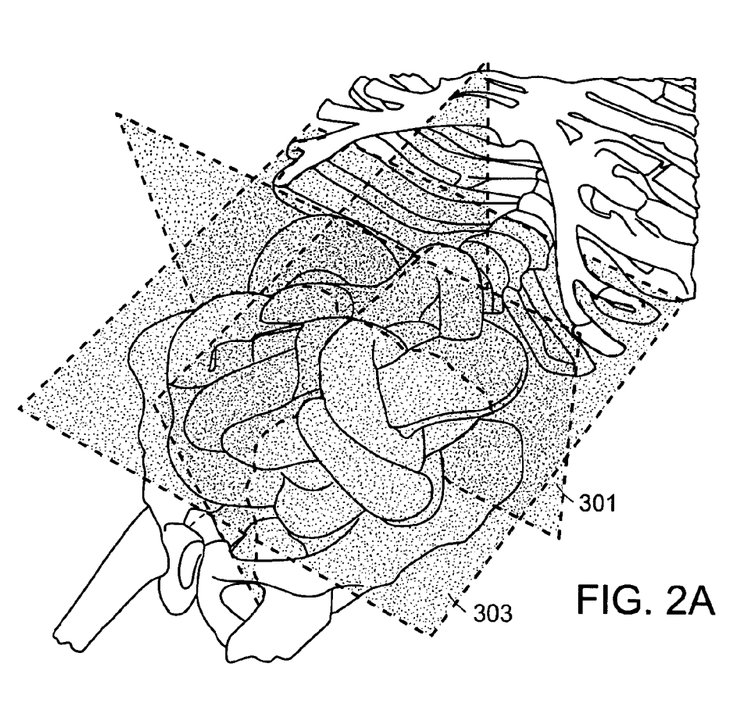
FIGS. 2A to B shows A) the dimensions of the abdominal cavity of an adult human on which the sizes of the device were based; and B) a front view of the device showing examples of possible dimensions of the device for use in an adult human.

FIG. 2A illustrates dimensions of the average human abdomen that were used to determine the dimensions of the device for use in adult human with the transverse 301 and coronal 303 planes indicated. Using the measurements of the adult human abdominal cavity and the devices of the invention, one can easily determine the appropriate dimensions for a device for use in a subject other than an adult human provided with the dimensions of the abdominal cavity (human child, dog, cat, other mammal). Anthropologic data was used to determine the small, medium, and large sizes designed to fit at least 95% of the adult human population. This flexibility of the device allows it to conform to cavities that may otherwise be too big or too small. In a preferred embodiment, the small size will be about 5.20 inches total in height and about 8.70 inches total in width; the large size will be about 7.50 inches in height and about 12.50 inches in length; the medium size of the device is about 6.53 inches in total height, including the body and flaps, and about 10.92 inches wide.

Figure 2B:
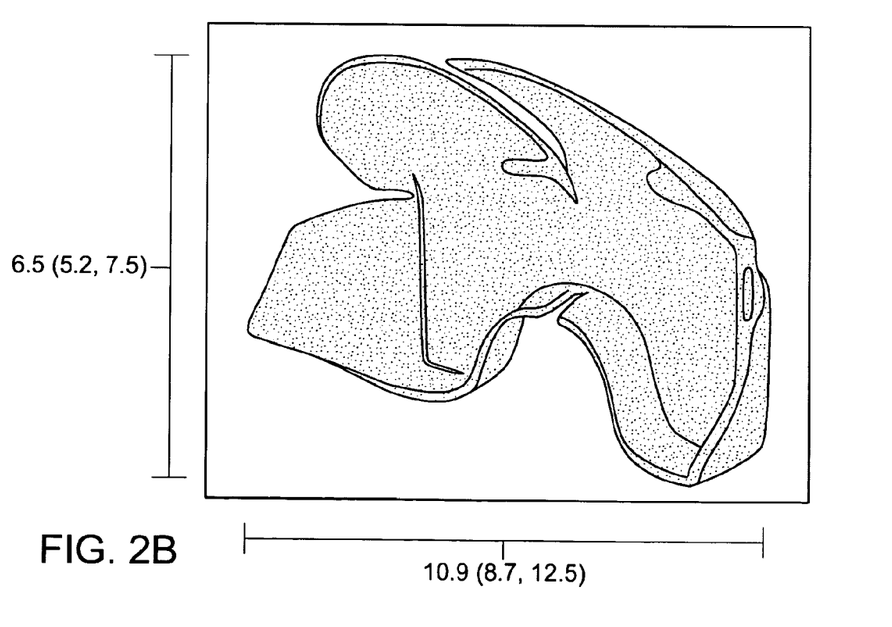

FIG. 2B shows a transparent view of an embodiment of a device of the invention showing examples of dimensions for the small, medium, and large adult human sizes.

The invention is designed to be interoperable with surgical retractor blades currently used during the bowel packing procedure. For incision sizes between 12 cm and 18 cm, it has been found that the device retains the bowels effectively for a 1-hour period without the support of retractor blades.

Additionally, the side and top flaps are designed to conform to the side and top of the abdominal cavity when packing cephally, to the pubic symphysis, so as to expose the lower pelvic cavity. Further the device can be modified to enable packing to be performed caudally so as to expose the upper and middle abdominal cavity. Thus, the device can be applied to a greater scope of abdominal and pelvic laparotomy procedures that require displacement of the bowels. Modification of the flap length and shape is within the ability of those of skill in the art based on the teachings provided herein.

The invention provides methods and the use of a device of the invention for achieving certain desirable outcomes during surgery. For example, the use of an elastomeric device of the instant invention provides advantages over laparotomy sponges not only in ease of use, but in improved patient outcomes, such as maintenance of intra-abdominal temperature and moisture during surgical procedures as demonstrated in the Examples below. The use of the devices of the invention provides a method for observation of the packed bowel during surgery as the device of the invention is preferably clear. During surgery, the bowel can be observed through the device for discoloration, bleeding, or other undesirable events.

Use of devices of the invention also provide for a reduction in adhesion formation as a result of bowel packing as compared to bowel packing performed with laparotomy sponges. Adhesions are due at least in part to fibers from laparotomy sponges that remain in the abdominal cavity after the removal of sponges at the end of the surgery. As the device of the invention includes no exposed fibers, none can be left behind, eliminating at least one substantial cause of adhesions. The device also reduces the possibility of medical errors as the device is a single piece that would be difficult to overlook at the conclusion of a surgical procedure, unlike a laparotomy sponge.

The use of the devices of the invention also provide a method to decrease bowel packing time and in longer surgeries the number of times that the bowel needs to be packed, thereby decreasing surgical time. The overall surgical time reduction will depend on the total surgical time and the number of times the bowel would need to be packed. However, the invention provides methods to reduce bowel packing time by at least 10%, at least 20%, at least 25%, at least 30%, or at least 35% as compared to bowel packing with laparotomy sponges.

Example 1

Manufacture of a Device of the Invention

The prototype device of the invention was cast using a combination silicone and Plaster of Paris™ mold. PDMS Sylgard® 186 was used to increase tear resistance of the device. The main body of the device was reinforced with PDMS Sylgard® 184 to prevent buckling upon application of shear and transverse forces by surgical retractor blades. The current prototype was scaled to fit a medium-sized human adult based on dimensions obtained from anthropologic data of pelvic size distributions.

Example 2

Material Testing Results

Two exemplary materials were tested to select the better material and the appropriate ratio of cross-linker for casting of a prototype. The device of the invention can be made of any elastomeric material having the desired elastic modulus, compression, and tear resistance and strength that can be sterilized, and that is preferably clear or at least translucent. Determination of properties of materials for making the device in the invention can be determined empirically using routine methods such as those provided below. Alternatively, the properties of the materials are commonly provided in catalogs, specification sheets, technical bulletins, and other manufacturer's information. Preferred materials for use for the device of the invention have a Young's modulus between 0.1 MPa and 10 MPa and a yield point of 250 KPa-5 Mpa. Materials should be tear resistant when subjected to 100 N of shear force. A single round of sterilization should not cause the material to lose these properties. The elastomeric polymer for manufacture of the device of the invention can include more than one polymer, either a mixture of polymers, different polymers for different portions of the device, or coating one polymer with another polymer. Such selections are a matter of choice and can be made by one of ordinary skill in the art.

1. Determination of Elastic Modulus

The elastic moduli of Sylgard® 184 and Sylgard® 186 were tested using routine methods to determine if the materials have elastic moduli in a range that offers sufficient flexibility for ease of insertion of the device and sufficient rigidity of the device to effectively retain the bowels. The target range of elastic moduli was between 0.1 MPa and 10 MPa. Base to cure ratios of Sylgard® 186 were varied in order to further explore the possible ranges of elastic modulus values that can be obtained. In addition, stress-strain curves were determined to determine the yield point of each material.

Figure 3A:
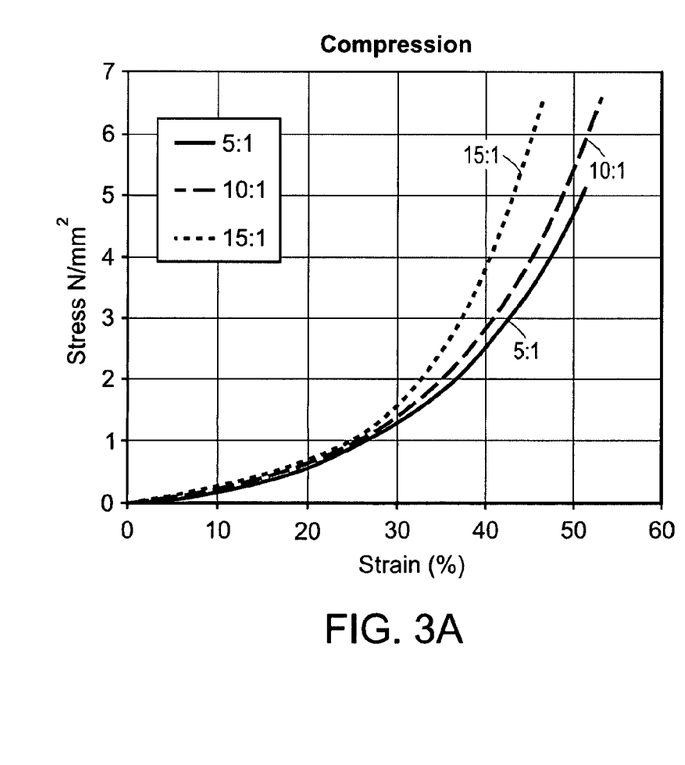
FIGS. 3A and B show the results from compression and tension tests performed on various silicon polymers.
Figure 3B:
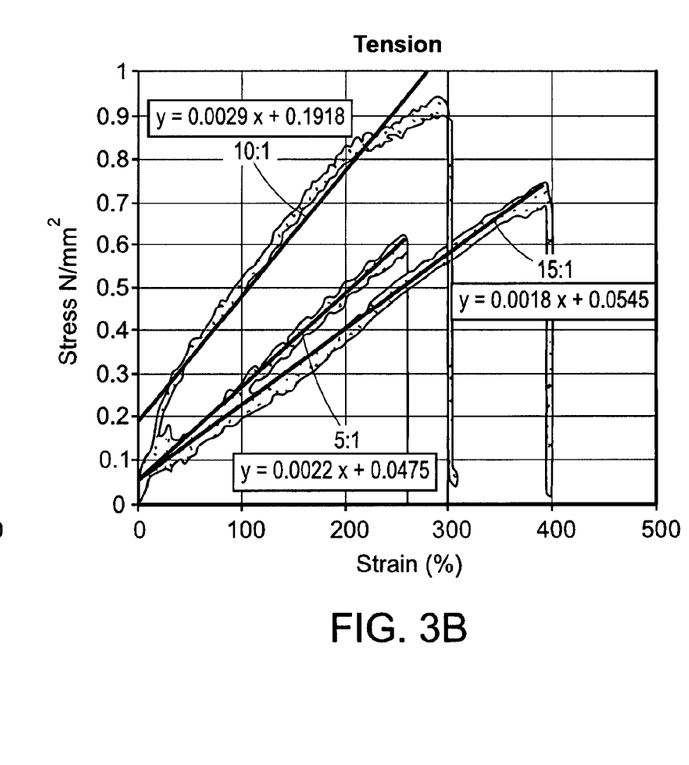

Five samples each measuring 2"×2" of Sylgard® 184 and 186 were tested and results averaged. The test equipment included an ATS (Applied Test Systems®; Butler, Pa.) Series 1601 and a Computer-Controlled Universal Test Machine (UTM). The results obtained are provided in FIGS. 3A and B.

It was determined that Sylgard® 184 and 186 have elastic moduli of 3.4 KPa and 2.9 KPa respectively; this falls within the range appropriate for use in devices of the invention. Because of its increased yield point of 900 KPa versus 500 KPa, Sylgard® 186 was identified as a better material choice than Sylgard® 184. Finally, a base to cure ratio of 10:1 was chosen for Sylgard® 186 because this ratio exhibited the highest elastic modulus of the samples tested. However, it was well below the lowerlimit of 0.1 MPa.

2. Determination of Tear Resistance and Tear Strength

Tear resistance is the resistance of a material to initial tearing while tear strength represents the force required to tear a pre-slit material. An un-slit material needs to have no visible tears develop upon application of 100 N of shear force. The amount of shear force required to tear pre-slit material was also determined to further understand one possible failure mode of the device. In order to determine if Sylgard® 184 and or Sylgard® 186 would be able to withstand the shear forces applied by the retractor blades on the body of the device, both tear resistance and tear strength of the material were determined. Sylgard® 184 and 186 were compared to determine the most tear-resistant material. Force thresholds were determined from measurements made in a simulated abdominal cavity.

Figure 4:
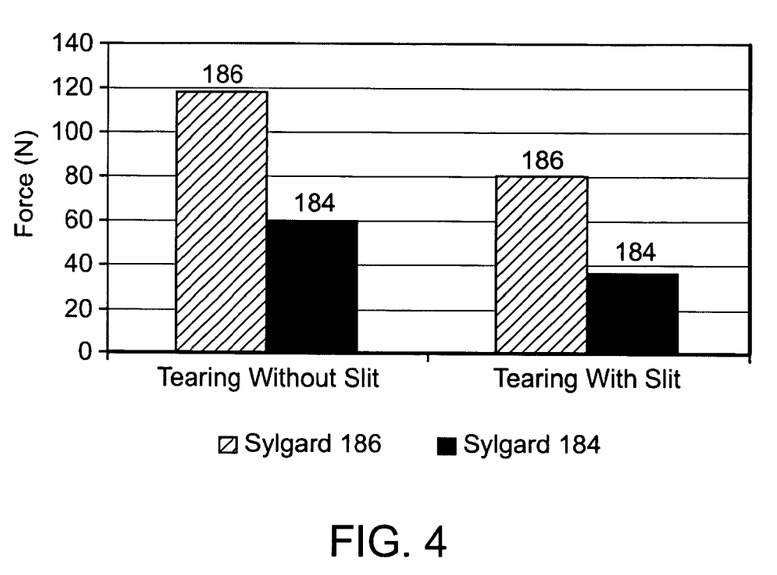
FIG. 4 shows the results from tearing tests performed on various silicon polymers.

The tear resistance of the material was tested by attaching the sample to one end of a dynamometer. The other end of the dynamometer was kept stationary. A shearing force was applied and gradually incremented. The peak reading of the dynamometer was recorded before the piece tore. When testing tear strength. a ⅛" incision perpendicular to the edge surface was made and the same shearing force was applied and incremented. Five samples of each material were used and the results were averaged and are shown in FIG. 4. As shown, Sylgard® 186 demonstrated greater tear resistance using both the intact and the slit sample.

3. Determination of Sterilization Resiliency

Samples of Sylgard® 186 were subjected to ten cycles of heat sterilization by autoclaving. It was determined that the tensile and compressive properties of Sylgard® 186 exhibited a 9.3% decrease in elastic modulus after ten sterilization cycles. Therefore, the elastic modulus remains within in an appropriate range for use in the method of the invention of less than 10%.

Example 3

Porcine Testing Results Comparing Laparotomy Packs to a Device of the Invention

Bowel Packing Time

Figure 5A:
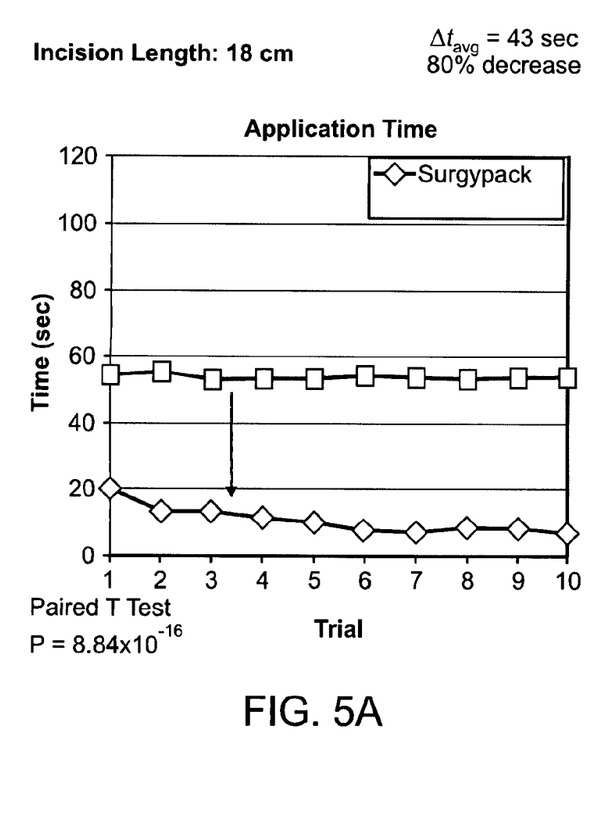
FIGS. 5A and B show the results from tests comparing bowel packing time of cotton laparotomy packs and the device of the invention in pigs with a 18 cm vertical incision or a 12 cm vertical incision.
Figure 5B:
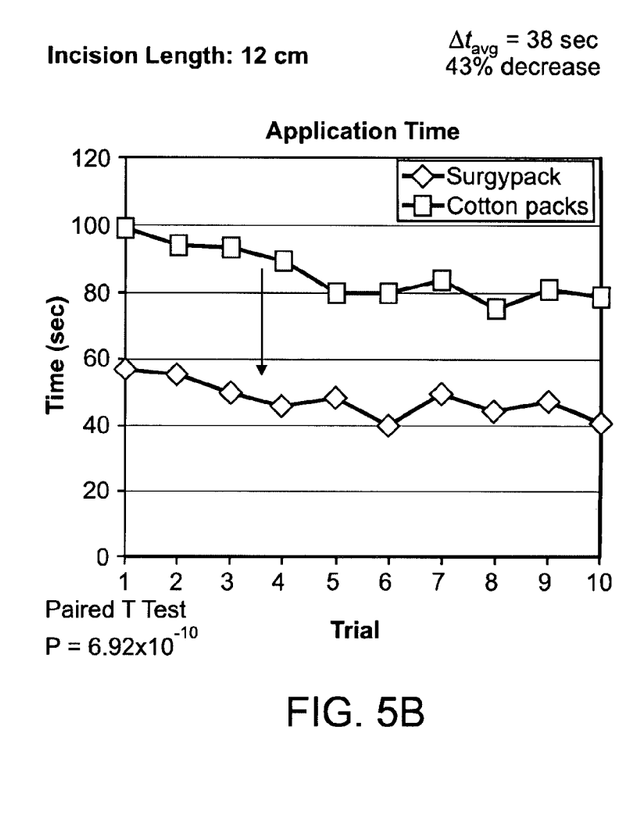

The time required for application of the device as well as its effectiveness in retaining the bowels versus the currently used cotton laparotomy packs was quantified in the porcine animal model. Two pigs were used to test the device's effectiveness. Before applying the device, the surgeon was given only a brief explanation of how the device was to be oriented in the cavity and that bowels were to be packed cephally. Once the pigs were fully anesthetized, a ventral midline incision was made to expose the abdominal contents. The incision was retracted using surgical retractor blades. The time required to apply the device and the cotton laparotomy packs each were recorded for a series of trials of bowel packing with the device or cotton laparotomy packs. As shown in FIGS. 5A and 6B, packing time was significantly decreased through both an 18 cm and a 12 cm incision (80% and 43%, respectively). This demonstrates that use of the device of the invention can reduce surgical times when bowel packing is required. In addition, the device can be removed by inserting one finger in the notch and lifting upward, eliminating the time required to remove individual laparatomy packs as well as eliminating the risk of a retained laparatomy pack.

Maintenance of Intra-Abdominal Temperature

Figure 6:
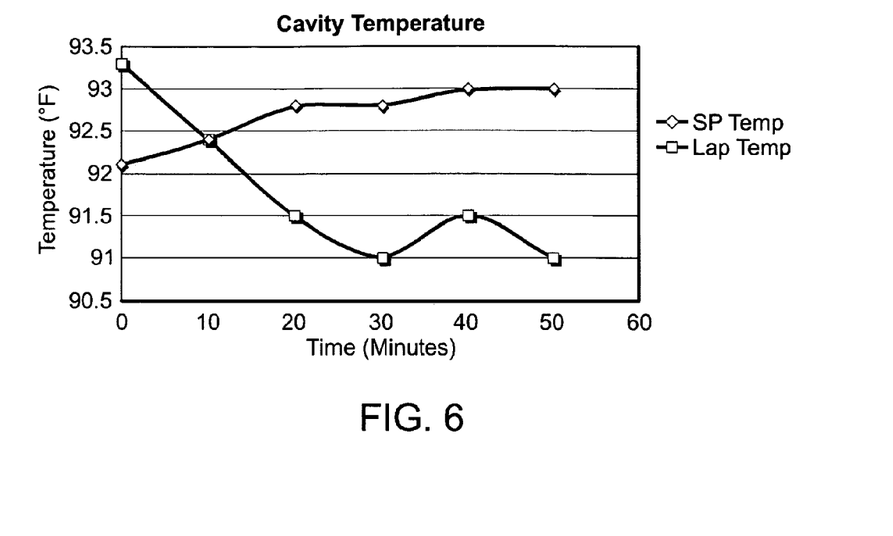
FIG. 6 shows the bowel retention time using cotton laparotomy packs (■) and a device of the invention (●).

Bowel packing was performed using a device of the invention or laparotomy packs through a 12 or 18 cm incision. Intra-abdominal temperature was measured upon the completion of bowel packing at six times at 10 minute intervals thereafter. Results are shown in FIG. 6. During the course of the experiment, cavity temperature decreased in the pig in which abdominal packing was performed with laparotomy pads, resulting in an abdominal cavity temperature about 7° C. below body temperature at the end of the experiment. Conversely, bowel packing with the device of the invention resulted in an increase in abdominal cavity temperature over the course of the experiment bringing cavity temperature to about 4.5 degrees below body temperature after 40 minutes of bowel packing with the device of the invention (n=1).

Maintenance of Bowel Retention

Bowel packing was performed using a device of the invention or laparotomy packs through a 12 or 18 cm incision. Bowel retention was observed at 5 minute intervals for a total of one hour under both static and dynamic conditions. The static phase of the test was conducted by leaving the packed bowels in the fully anesthetized animal, undisturbed by the surgeon. The device is only subject to the forces produced by the animal's physiological processes.

The dynamic phase of the test began with the surgeon performing a nephrectomy. Attempts to dislodge the device included grasping the animal by the pelvis and shaking the abdomen.

Bowels are considered to have entered the surgical field (i.e., no longer be retained) once a segment greater than 1 cm in length breaks the plane formed by extending the surface of the device nearest the surgical field.

Figure 7:
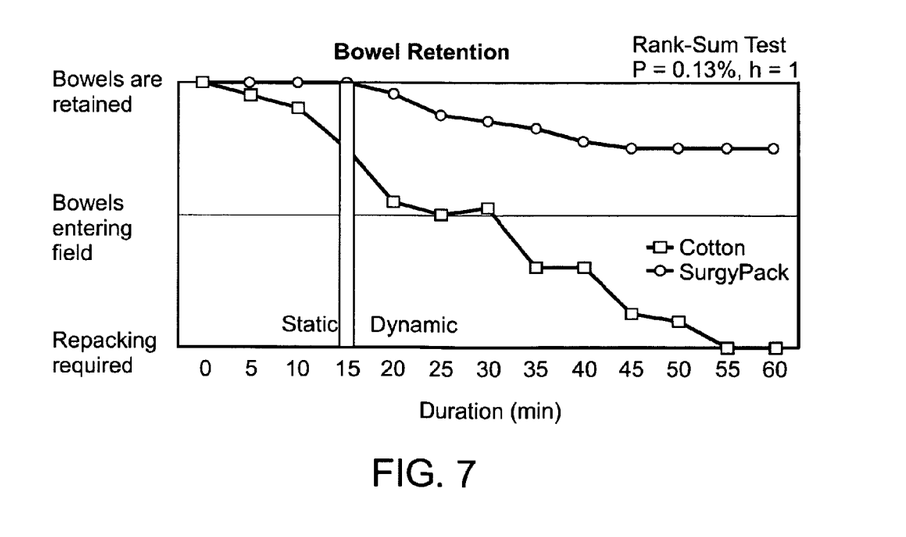
FIG. 7 shows the change in intra-abdominal temperature over time with cotton laparotomy packs (■) and a device of the invention (♦).

The device of the invention was found to retain the bowels throughout the course of the experiment, whereas the significant bowel leakage occurred with the laparotomy packs after as little as 15 minutes with bowels entering the field at 20 minutes (FIG. 7). After less than one hour, repacking was required after packing with laparotomy packs. These data demonstrate that the device of the invention provides better bowel retention than standardly used laparotomy packs.

Those skilled in the art will recognize, or be able to ascertain using no more than routine experimentation, many equivalents to the specific embodiments of the invention described herein. Such equivalents are intended to be encompassed by the following claims.

All references, patents, and patent publications cited herein are incorporated herein by reference

We claim:

1. A device for bowel packing comprising:
   an essentially elliptically-shaped device essentially symmetrical along a minor axis of the ellipse;
   wherein the ellipse comprises a perimeter, minor axis comprising a length, and a major axis comprising a length;
   wherein the essentially elliptically-shaped device comprises at least four radial notches in the perimeter comprising:
   (a) one or more radial notches arranged above the major axis, wherein each notch comprises a length from the center of the notch at the perimeter to a base of the notch, wherein the notch length comprises about 30% to about 40% of the length of the minor axis and each notch comprises a width at the perimeter of the ellipse comprising about 10% to about 15% of a length of a major axis of the ellipse;
   (b) a second radial notch located on the minor axis below the major axis wherein the second notch comprises a length from the perimeter to a top of the notch of about 30% to about 40% of the length of the minor axis and a width at the perimeter of about 32% to about 42% of the length of the major axis;
   (c) two or more radial notches arranged left and right of the minor axis wherein each notch comprises a length from the center of the notch at the perimeter to a base of the notch of at least about 5-15% of the length of the major axis;
   wherein the device is composed of material comprising an elastomeric compound and the device is appropriately sized for retaining the intestines of a mammal; and
   wherein the elastomeric compound comprises an elastomeric polymer having an elastic modulus of about 0.1 MPa to about 10 MPa.

2. The device of claim 1 wherein the ratio of the length of the minor axis of the ellipse to the length of the major axis of the ellipse is about 0.55 to about 0.65.

3. The device of claim 1 wherein the one or more radial notches of (a) comprises one radial notch.

4. The device of claim 1, wherein the two or more radial notches of (c) comprise one radial notch to the left of the minor axis and one radial notch to the right of the minor axis.

5. The device of claim 1, wherein the radial notches of (c) are located at or above the major axis.

6. The device of claim 1, wherein the device is essentially concave.

7. The device of claim 1, wherein the device comprises a bend near the line between two essentially symmetrically positioned radial notches of (c).

8. The device of claim 1, wherein the device comprises a bend near a line parallel with the major axis along a line near the top of a bottom radial notch.

9. The device of claim 1, wherein the shape of the at least four radial notches is independently selected from the group consisting of V-shaped, U-shaped, and bell-shaped.

10. The device of claim 1, wherein the thickness of the device at an intersection of the major axis and the minor axis is greater than the thickness of the device at the perimeter.

11. The device of claim 1 further comprising a coating.

12. The device of claim 11, wherein the coating comprises a compound selected from the group consisting of chemically modified hyaluronic acid and carboxymethylcellulose, oxidized regenerated cellulose, rapamycin, (2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate, dihydroxy-12-[(2R)-1-[(1S,3R,4R)-4-(2-hydroxyethoxy)-3-methoxycyclohexyl] propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone, 2-{[(2E)-3-(3,4-dimethoxyphenyl)prop-2-enoyl] amino}benzoic acid, polyethylene terephthalate, polytetrafluoroethylene, collagen matrix, bioresorbable polymeric film composed of poly-lactic acid (PLA) and polyethylene glycol (PEG), icodextrin, hyaluronic acid, heparin, dextran, tissue plasminogen activator, corticosteroids, non-steroid inflammatory drugs (NSAIDS) such as ibuprophen, chondroitin sulfate, carboxymethylcellulose, dexamethosane, tissue plasminogen including recombinant tissue plasminogen, oxyphenbutazone, collagen, collagen inhibitors, polylactic acid, polyglycolic acid, alginic acid, polycaprolactone, glycosaminoglycans, polyethylene oxide (PEO), polyethylene oxide-polypropylene oxide copolymer in any monomeric ratio (PEG-PPO-PEG), hydroxy ethyl methyl acrylate (HEMA), poly(N-isopropylacrylamide) (NIPAAm), polytetrafluoroethylene (PTFE), polyesters, and silane, or modification by radio frequency gas discharge (RFGD), and radiation grafting, polytetrafluoroethylene (PTFE), polylactic acid, polyglycolic acid, alginic acid, polycaprolactone, glycosaminoglycans, HEMA, ePTFE, polyesters, carboxymethylcellulose, dexamethasone, tissue plasminogen including recombinant tissue plasminogen, oxyphenbutazone, corticosteriods, icodextrin, hyaluronic acid, hyaluronan, collagen inhibitors, and silane and modification radio frequency gas discharge (RFGD), and radiation grafting.

13. The device of claim 12, wherein the device is essentially concave.

14. The device of claim 1, wherein the device comprises a bend along a line near the top of the notch of (b).

15. The device of claim 1, wherein the shape of the radial notches are independently selected from the group consisting of V-shaped, U-shaped, and bell-shaped.

16. The device of claim 1, wherein the elastomeric compound comprises a compound selected from the group consisting of silicone, liquid silicone rubber (LSR), polydimethylsiloxane (PDMS), styrene butadiene rubber, styrene butadiene styrere (SBS) rubber, nitrile rubber, and polychloroprene.

17. The device of claim 1, wherein the elastomeric compound comprises a composite of an elastomeric compound.

18. The device of claim 1, wherein the device comprises a fiber encased within the elastomeric compound.

19. The device of claim 1, wherein the device comprises a radio-opaque substance.

20. A device for bowel packing comprising:
an essentially elliptically-shaped device essentially symmetrical along a minor axis of the ellipse
wherein the ellipse comprises a minor axis comprising a length and a major axis comprising a length;
wherein the device comprises an essentially rectangular body comprising a first long edge opposite a second long edge and a first short edge and a second short edge wherein the first and second short edge separate the long edges; wherein
  a) the first long edge is contiguously joined along the length of the first long edge to a top flap comprising a height and a width, wherein the top flap comprises a first cutout from an edge of the flap opposite the long edge of the body to which the flap is attached, wherein the depth of the first cutout comprises at least 80% of the height of the top flap;
  b) the second long edge is contiguously joined along the length of the second long edge to a bifurcated bottom flap wherein each half of the bifurcated bottom flap comprises a height and a width wherein the height and the width of each half flap is essentially the same as the height and width of the other half flap, and the width of the flap extends about 10 to 20% beyond the length of the second long edge of body of the device on each side of the second long edge, wherein the bottom flap is bifurcated by a second cutout on an edge of the flap opposite the long edge of the body to which the bottom flap is attached wherein the width of the second cutout is about 30% to about 55% of the length of the long edge of the device and the second cutout is centered along the second long edge of the body of the device, and the height of the second cutout is about 25% to about 40% of a height of the device at the tallest point perpendicular to the first long edge of the body; and
  c) the first short edge contiguously is joined along the length of the first short edge to a first side flap and the second short edge is contiguously joined along the length of the second short edge to a second side flap wherein the first side flap and the second side flap comprise a height and a width, and the height and the width of the first side flap are about the same as the height and the width of the second side flap;
wherein the width of each side flap is about 10-20% of an overall width of the device,
wherein a lower edge of each side flap forms a smooth edge with a bottom half flap; the device is appropriately sized for bowel packing in a mammal; and the device is composed of material comprising an elastomeric polymer wherein the elastomeric polymer comprises an elastic modulus of about 0.1 MPa to about 10 MPa.

21. The device of claim 20, wherein the ratio of the short edge of the rectangular body to the long edge of the rectangular body is about 0.2 to about 0.3.

22. The device of claim 20, wherein the device comprises a bend near the line that forms the top of the rectangular body.

23. The device of claim 20, wherein the thickness of the rectangular body is greater than the thickness of the edges of the top, bottom, first side, and second side flaps away from the rectangular body.

24. The device of claim 20, wherein the thickness of the bifurcated bottom flap is greater than the thickness of the top flap.

25. The device of claim 20 further comprising a coating.

26. The device of claim 25, wherein the coating comprises a compound selected from the group consisting of chemically modified hyaluronic acid and carboxymethylcellulose, oxidized regenerated cellulose, rapamycin, ($2\alpha,4\alpha,5\beta,7\beta,10\beta,13\alpha$)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate, dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone, 2-{[(2E)-3-(3,4-dimethoxyphenyl)prop-2-enoyl]amino}benzoic acid, polyethylene terephthalate, polytetrafluoroethylene, collagen matrix, bioresorbable polymeric film composed of poly-lactic acid (PLA) and polyethylene glycol (PEG), icodextrin, hyaluronic acid, heparin, dextran, tissue plasminogen activator, corticosteroids, non-steroid inflammatory drugs (NSAIDS) such as ibuprophen, chondroitin sulfate, carboxymethylcellulose, dexamethosane, tissue plasminogen including recombinant tissue plasminogen, oxyphenbutazone, collagen, collagen inhibitors, polylactic acid, polyglycolic acid, alginic acid, polycaprolactone, glycosaminoglycans, polyethylene oxide (PEO), polyethylene oxide-polypropylene oxide copolymer in any monomeric ratio (PEG-PPO-PEG), hydroxy ethyl methyl acrylate (HEMA), poly(N-isopropylacrylamide) (NIPAAm), polytetrafluoroethylene (PTFE), polyesters, and silane, or modification by radio frequency gas discharge (RFGD), and radiation grafting, polytetrafluoroethylene (PTFE), polylactic acid, polyglycolic acid, alginic acid, polycaprolactone, glycosaminoglycans, HEMA, ePTFE, polyesters, carboxymethylcellulose, dexamethasone, tissue plasminogen including recombinant tissue plasminogen, oxyphenbutazone, corticosteriods, icodextrin, hyaluronic acid, hyaluronan, collagen inhibitors, and silane and modification radio frequency gas discharge (RFGD), and radiation grafting.

* * * * *